United States Patent [19]

Nakashima et al.

[11] Patent Number: 5,258,393
[45] Date of Patent: Nov. 2, 1993

[54] USE OF A DIHYDROPYRIDINE COMPOUND FOR IMPROVING INNER EAR MICROCIRCULATION

[75] Inventors: Mitsuyoshi Nakashima; Toshihiko Uematsu, both of Hamamatsu, Japan; Kazuo Umemura, Muttenz, Switzerland; Yutaka Kohno, Hamamatsu, Japan

[73] Assignee: Fujisawa Pharmaceutical Co., Ltd., Osaka, Japan

[21] Appl. No.: 798,061

[22] Filed: Nov. 27, 1991

Related U.S. Application Data

[63] Continuation of Ser. No. 658,293, Feb. 20, 1991, abandoned.

Foreign Application Priority Data

Feb. 21, 1990 [JP] Japan .................................. 2-40413
May 10, 1990 [JP] Japan ................................. 2-122110

[51] Int. Cl.$^5$ ............................................. A61K 31/44
[52] U.S. Cl. .................................................. 514/344
[58] Field of Search ..................................... 514/344

[56] References Cited

U.S. PATENT DOCUMENTS 4,782,070 11/1988 Ono et al. .......................... 514/344
5,032,601 7/1991 Ono et al. .......................... 514/344

FOREIGN PATENT DOCUMENTS 0322747 7/1989 European Pat. Off. .
0323604 7/1989 European Pat. Off. .

OTHER PUBLICATIONS

CA 110:33741k, Ono et al., 1988.
CA 100:61559u, Gross et al., 1983.
CA 100:167988y, Gross et al., 1984.
CA 107:217482w, Wehinger et al., 1987.
Eur. J. Pharmacol., vol. 183, No. 5, 1990, pp. 1839-1840; Y. Kohno et al.: "A new model of hearing loss due to the photochemically induced thrombosis in the inner ear microcirculation".

Primary Examiner—Frederick E. Waddell
Assistant Examiner—Kimberly R. Jordan
Attorney, Agent, or Firm—Oblon, Spivak, McClelland, Maier & Neustadt

[57] ABSTRACT

The invention relates to a method for improving inner ear microcirculation, which comprises administering an effective amount of a dihydropyridine compound of the general formula:

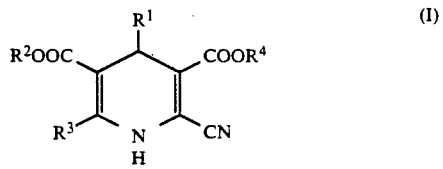

wherein $R^1$ is a nitrophenyl group; and
$R^2$, $R^3$ and $R^4$ each is a lower alkyl group, or a pharmaceutically acceptable salt thereof to a human or animal.

3 Claims, No Drawings

USE OF A DIHYDROPYRIDINE COMPOUND FOR IMPROVING INNER EAR MICROCIRCULATION

This application is a continuation of application Ser. No. 07/658,293, filed on Feb. 20, 1991, now abandoned.

This invention relates to new use of a dihydropyridine compound for improving an inner ear microcirculation.

In more detail, this invention relates to new use of the dihydropyridine compound (I), which can be represented by the following general formula, or a pharmaceutically acceptable salt thereof for improving an inner ear microcirculation.

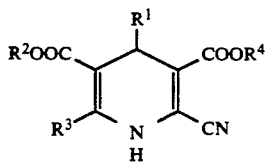

wherein $R^1$ means a nitrophenyl group; $R^2$, $R^3$ and $R^4$ each means a lower alkyl group.

The dihydropyridine compound (I) used in this invention is known as described in, inter alia, British Patent No. 2,036,722. It is also known that pharmacologically this dihydropyridine compound (I) has a vasodilating action based on calcium ion antagonism and as such is of value as an antianginal or antihypertensive agent, as a cerebral circulation improving agent and further as an antiarteriosclerotic agent.

The intensive research done by the inventors of this invention revealed that said dihydropyridine compound (I) and its pharmaceutically acceptable salts have, in addition to the aforesaid actions, an action to improve an inner ear microcirculation. This finding provided a basis for this invention.

The inner ear microcirculation improving action of the dihydropyridine compound (I) and its pharmaceutically acceptable salts is considered to be a novel pharmacologic action based on inhibition of the formation of microthrombi, which are considered to be a major causative factor in disorder of inner ear microcirculation, and on the prevention of vasospasms and, as such, should be regarded as being pharmacologically distinct from the various effects mentioned above.

Accordingly it is an object of this invention to provide new method for improving the inner ear microcirculation, which comprises administering an effective amount of the dihydropyridine compound (I) or a pharmaceutically acceptable salt thereof for the prophylaxis and treatment of diseases associated with disorder of inner ear microcirculation.

It is further object of this invention to provide new use of the dihydropyridine compound (I) or a neopentyl, 1- or 2-methylbutyl and hexyl. Preferred are $C_{1-4}$ alkyl groups. The most preferred example of $R^2$ is isopropyl, while methyl is the most preferred example of $R^3$ and $R^4$.

The inner ear microcirculation improving agent of this invention can be administered, orally or otherwise, to man and other mammalian animals, in any of the conventional pharmaceutical dosage forms such as capsules, microcapsules, tablets, granules, powders, troches, pills, ointments, suppositories, injections, syrups and so on.

The inner ear microcirculation improving agent can be manufactured by the established pharmaceutical procedures using ordinary organic or inorganic carriers which are well known in the art. These carriers include, inter alia, various excipients such as sucrose, starch, mannitol, sorbitol, lactose, glucose, cellulose, talc, calcium phosphate, calcium carbonate, etc.; binders such as cellulose, methylcellulose, hydroxymethylcellulose, polypropylpyrrolidone, gelatin, gum arabic, polyethylene glycol, sucrose, starch, etc.; disintegrating agents such as starch, carboxymethylcellulose, hydroxypropylstarch, sodium hydrogen carbonate, calcium phosphate, calcium citrate, etc.; lubricants such as magnesium stearate, Aerosil, talc, sodium laurylsulfate, etc.; flavoring agents such as citric acid, menthol, glycine, orange powder, etc.; preservatives such as sodium benzoate, sodium bisulfite, methylparaben, propylparaben, etc.; stabilizers such as citric acid, sodium citrate, acetic acid, etc.; suspending agents such as methylcellulose, polyvinylpyrrolidone, aluminum stearate, etc.; dispersing agents such as hydroxypropylmethylcellulose etc.; diluents such as water etc.; and base waxes such as pharmaceutically acceptable salt thereof as an inner ear microcirculation improving agent.

It is still further object of this invention to provide an inner ear microcirculation improving agent containing an effective amount of the dihydropyridine compound (I) or a pharmaceutically acceptable salt thereof.

It is also an object of this invention to provide new use of the dihydropyridine compound (I) or a pharmaceutically acceptable salt thereof for manufacturing a medicament for improving the inner ear microcirculation.

Among the diseases which are induced by disorder of inner ear microcirculation are, for example, deafness, dizziness, and the like.

The pharmaceutically acceptable salt mentioned above includes nontoxic salts of the known types, for example salts with inorganic bases such as alkali metals (e.g. sodium, potassium, etc.), alkaline earth metals (e.g. calcium, magnesium, etc.), ammonium, etc., and salts with organic bases such as organic amines (e.g. triethylamine, pyridine, picoline, ethanolamine, triethanolamine, dicyclohexylamine, N,N'-dibenzylethylenediamine, etc.).

Referring to the general formula (I) presented above, preferred examples of $R^1$, $R^2$, $R^3$ and $R^4$ are as follows.

As examples of the nitrophenyl $R^1$, there may be mentioned 2-nitrophenyl, 3-nitrophenyl and 4-nitrophenyl, and among them, 3-nitrophenyl is particularly preferable.

As examples of the lower alkyl group independently presented by $R^2$, $R^3$ and $R^4$, there may be mentioned $C_{1-6}$ alkyl groups, such as methyl, ethyl, propyl, isopropyl, butyl, isobutyl, sec.-butyl, pentyl, isopentyl, cacao butter, white petrolatum, polyethylene glycol and so on.

The dosage of the active ingredient of the dihydropyridine compound (I) depends on such factors as the body weight, age of the patient, the severity of the disease and administration routes. Generally speaking, however, the inner ear microcirculation improving agent of the invention is administered orally in a daily dose of 0.5 to 1000 mg, preferably 1 to 500 mg, as the dihydropyridine compound (I). The unit dose is selected from the range of 0.01 to 20 mg, preferably 0.05 to 2 mg, per kilogram body weight.

The following pharmacological test data indicate the usefulness of the dihydropyridine compound (I) or a pharmaceutically acceptable salt thereof which is employed in the inner ear microcirculation improving agent of this invention.

Test 1

Method

Male Wistar rats (body weights 240–260 g) were anesthetized with pentobarbital. After tracheotomy, the animals were artificially ventilated with a Harvard 683 respirator. A solution of Rose Bengal (RB) in saline (10 mg/ml) was infused into the femoral vein at a speed of 24 μmoles/kg per hour. After initiation of Rose Bengal infusion, the left middle ear was opened and, for electrocochleography, the round window lead electrode was fixed in position. Thus, after incision of the skin and muscle of the neck region, the tympanic cavity was drilled with a miniature dill and a silver ball electrode was placed on the round window membrane for use as an active electrode. An indifferent electrode was placed in the middle of the back of the head. Thirty minutes after initiation of Rose Bengal infusion, the lateral wall of the cochlea was irradiated with a green light (540 nm) conducted from a light source (L-3306-01A, Hamamatsu Photonics) through an optical fiber. Using a manipulator, the free end of the optical fiber was fixed about 5 mm away from the lateral wall of the cochlea. In this arrangement, the compound action potential (CAP) was recorded at 1-minute intervals. The electrocochleogram was recorded with Nihon Kohden Neuropack II by averaging 128 clicks of 8 kHz at a sound pressure level of 100 dB. The vehicle (polyethylene glycol(400)-water, 1:1 v/v) or the test compound (dissolved in the vehicle) was injected intravenously 10 minutes prior to photoillumination.

Test compound

Isopropyl 6-cyano-5-methoxycarbonyl-2-methyl-4-(3-nitrophenyl)-1,4-dihydropyridine-3-carboxylate (hereinafter referred to as dihydropyridine compound A)

| Dosage (mg/kg) | Result | |
|---|---|---|
| | Number of animals | Action potential disappearance time (min.) |
| 0 (Vehicle only) | 8 | 12.0 |
| 0.3 | 6 | 14.5 |

Histologically, damage to the stria vascularis of the lateral wall was found after 1 hour of photoillumination and complete disintegration of the inner hair cells was observed after 24 hours. These findings were characteristic ischemic changes of the inner ear similar to those reported by Robert Kimura (Annals of Otology, Rhinology and Laryngology 67, 6–24, 1958). The ischemic changes were verified morphologically. The fact that pretreatment with heparin (5 min. before the photoillumination) prolonged the time required to diminish the AP suggests that the diminution of the AP is caused by the impairment of inner ear microcirculation due to the microthrombus formed following injury of the vascular endothelial cells.

Test 2

Method

Rats were anesthetized with pentobarbital, and with the body temperature maintained at 37° C. with a heating pad, an aqueous solution of Rose Bengal was continuously infused into the femoral vein. The inner ear was then opened and the tympanic membrane, incus and malleus were removed taking care not to impair the inner ear.

Using a Hamamatsu Photonic xenon lamp, the oval window was irradiated with a green light of 540 nm via an optical fiber. Using a manipulator, the end of the fiber was fixed about 3 mm from the lateral wall of the cochlea.

Photoillumination was started 20 minutes after the beginning of Rose Bengal infusion and a solution of the test compound in polyethylene glycol (400)-water (1:1, v/v) was intravenously administered at the beginning of photoillumination. After 40 minutes of irradiation, both the photoillumination and Rose Bengal infusion were terminated, the wound was sutured, and the animal was allowed to regain consciousness. At 24 hours after termination of photoillumination, a nystagmus test and a swimming test for imbalance were performed.

Test compound

Dihydropyridine compound A

| Dosage (mg/kg) | Number of test animals | Result | |
|---|---|---|---|
| | | Incidence (%) | |
| | | Nystagmus | imbalance |
| 0 | 16 | 100 | 100 |
| 0.03 | 12 | 58.3 | 58.3 |

It is apparent from the above results that dihydropyridine compound A improves disorder of inner ear microcirculation to prolong the action potential (AP) disappearance time and inhibit onset of nystagmus and imbalance, thus being of value as an inner ear microcirculation improving agent.

The following examples are further illustrative of the invention.

EXAMPLE 1

| Dihydropyridine compound A | 100 g |
|---|---|
| Hydroxypropylmethylcellulose | 500 g |

In absolute ethanol (5 liters) is dissolved dihydropyridine compound A followed by addition of hydroxypropylmethylcellulose to provide a suspension. The organic solvent is then distilled off under reduced pressure to give a solid dispersion.

EXAMPLE 2

| Dihydropyridine compound A | 100 g |
|---|---|
| Hydroxypropylmethylcellulose | 500 g |
| Sucrose | 9.4 kg |

In absolute ethanol (5 liters) are suspended dihydropyridine compound A and hydroxypropylmethyl cellulose followed by addition of sucrose and the mixture is stirred. The organic solvent is then distilled off under reduced pressure to provide a solid dispersion. This dispersion is processed into fine granules by the established pharmaceutical procedure.

EXAMPLE 3

| | |
|---|---|
| Dihydropyridine compound A | 100 g |
| Hydroxypropylmethylcellulose | 500 g |
| Lactose | 6.87 kg |
| Low-substituted hydroxypropylcellulose | 1.5 kg |
| Magnesium stearate | 30 g |

In absolute ethanol (5 liters) are suspended dihydropyridine compound A and hydroxypropylmethylcellulose followed by addition of lactose and low-substituted hydroxypropylcellulose and the resulting mixture is stirred. The organic solvent is then distilled off under reduced pressure to give a solid dispersion. This dispersion is granulated by the routine procedure and, after addition of magnesium stearate, the granulation is compressed into tablets in the routine manner. Each of these tablets contains 2 mg of dihydropyridine A.

EXAMPLE 4

The tablets prepared in Example 3 were respectively film-coated by the routine procedure using a coating composition comprising hydroxypropylmethylcellulose (5.1 mg), titanium dioxide (1.6 mg), polyethylene glycol 6000 (0.8 mg), talc (0.4 mg) and yellow iron oxide (0.1 mg) to provide film-coated tablets, each containing 2 mg of dihydropyridine compound A.

EXAMPLE 5

The racemate of methyl 5-carboxy-2-cyano-6-methyl-4-(3-nitrophenyl)-1,4-dihydropyridine-3-carboxylate (16.7 g) and cinchonidine (14.4 g) are dissolved in methanol (100 ml) and the solution is refluxed for 15 minutes. The reaction mixture is then allowed to stand at ambient temperature. The resulting precipitate is recovered by filtration, washed with methanol and dried in the air to give methyl (−)-5-carboxy-2-cyano-6-methyl-4-(3-nitrophenyl)-1,4-dihydropyridine-3-carboxylate cinchonidine salt (11.74 g).

The mother liquor is distilled under reduced pressure to remove the solvent. The crystalline residue is washed with a mixture of ethyl acetate and diisopropyl ether, diluted with 2N hydrochloric acid (40 ml) and extracted with ethyl acetate. The extract is washed with aqueous sodium chloride solution, dried over anhydrous magnesium sulfate and distilled under reduced pressure to remove the solvent. The procedure gives a mixture of (+)- and (−)-isomers of methyl 5-carboxy-2-cyano-6-methyl-4-(3-nitrophenyl)-1,4-dihydropyridine-3-carboxylate (11.15 g).

This mixture (11.15 g) and cinchonine (9.54 g) are dissolved in ethyl acetate with heating and the solution is allowed to stand at ambient temperature. The resulting precipitate is collected by filtration, washed with ethyl acetate and recrystallized from ethanol. The procedure gives methyl (+)-5-carboxy-2-cyano-6-methyl-4-(3-nitrophenyl)-1,4-dihydropyridine-3-carboxylate cinchonine salt (7.62 g).

m.p.: >164° C. (decompn.).

$[\alpha]_D^{20}$: +243.2° (c=1.0, CH$_3$OH).

EXAMPLE 6

In ethyl acetate (50 ml) is suspended methyl (+)-5-carboxy-2-cyano-6-methyl-4-(3-nitrophenyl)-1,4-dihydropyridine-3-carboxylate cinchonine salt (7.41 g) followed by addition of 2N hydrochloric acid (20 ml) with stirring, and the water layer is then removed. The organic layer is washed with aqueous sodium chloride solution, dried over magnesium sulfate and distilled under reduced pressure to remove the solvent. The procedure gives methyl (+)-5-carboxy-2-cyano-6-methyl-4-(3-nitrophenyl)-1,4-dihydropyridine-3-carboxylate (3.67 g).

m.p.: 203° C. (decompn.).

$[\alpha]_D^{20}$: +234.1° (c=1.0, CH$_3$OH).

NMR (DMSO-d$_6$, δ): 2.34 (3H, s), 3.71 (3H, s), 5.13 (1H, s), 7.56–7.82 (2H, m), 7.91–8.25 (2H, m), 10.25 (1H, broad s),

EXAMPLE 7

In methylene chloride (30 ml) is suspended methyl (+)-5-carboxy-2-cyano-6-methyl-4-(3-nitrophenyl)-1,4-dihydropyridine-3-carboxylate (3.12 g) followed by addition of phosphorus pentachloride (2.46 g) with ice-cooling, and the mixture is stirred for 30 minutes. Then, a solution of isopropyl alcohol (1.4 g) in methylene chloride (10 ml) is added dropwise over a period of 10 minutes. The mixture is stirred for 20 minutes, at the end of which time 5% aqueous sodium carbonate solution (30 ml) is added and the mixture is stirred at ambient temperature for one hour. The organic layer is separated and the water layer is extracted with methylene chloride. The organic layers are combined, washed with aqueous sodium chloride solution, dried over anhydrous magnesium sulfate and distilled under reduced pressure to remove the solvent. The residue is purified by silica gel (75 g) column chromatography, elution being carried out with benzeneethyl acetate (10:1). The solvent is removed from the eluate under reduced pressure and the residue is crystallized from diisopropyl ether to provide 5-isopropyl 3-methyl (+)-2-cyano-6-methyl-4-(3-nitrophenyl)-1,4-dihydropyridine-3,5-dicarboxylate (3.34 g).

m.p.: 120°–122° C.

$[\alpha]_D^{20}$: +222.4° (c=1.0, CH$_3$OH).

NMR (CDCl$_3$, δ): 1.09 (3H, d, J=6.5 Hz), 1.26 (3H, d, J=6.5 Hz), 2.40 (3H, s), 3.76 (3H, s), 4.97 (1H, heptet, J=6.5 Hz), 5.17 (1H, s), 6.96 (1H, broad s), 7.21–7.77 (2H, m), 7.95–8.21 (2H, m).

Elemental analysis: for C$_{19}$H$_{19}$N$_3$O$_6$: Calcd.: C 59.22; H 4.97; N 10.90; Found : C 59.38; H 5.08; N 10.98;

EXAMPLE 8

The methyl (−)-5-carboxy-2-cyano-6-methyl-4-(3-nitrophenyl)-1,4-dihydropyridine-3-carboxylate cinchonidine salt (11.74 g) prepared according to Example 5 is recrystallized from methanol to provide its pure compound (9.36 g).

m.p.: 159°–160° C.

$[\alpha]_D^{20}$: −198.9° (c=1.0, CH$_3$OH).

This compound (9.05 g) is suspended in ethyl acetate (50 ml) followed by addition of 2N hydrochloric acid (20 ml). The water layer is discarded. The organic layer is washed with aqueous sodium chloride solution, dried over anhydrous magnesium sulfate and evaporated under reduced pressure. The procedure gives methyl (−)-5-carboxy-2-cyano-6-methyl-4-(3-nitrophenyl)-1,4-dihydropyridine-3-carboxylate (5.11 g).

m.p.: 205° C. (decompn.).

$[\alpha]_D^{20}$: −230.7° (c=1.0, CH$_3$OH).

NMR (DMSO-d$_6$, δ): 2.34 (3H, s), 3.71 (3H, s), 5.13 (1H, s), 7.5614 7.82 (2H, m), 7.9114 8.23 (2H, m), 10.25 (1H, broad s).

EXAMPLE 9

Methyl (−)-5-carboxy-2-cyano-6-methyl-4-(3-nitrophenyl)-1,4-dihydropyridine-3-carboxylate (4.47 g) is reacted with phosphorus pentachloride (3.62 g) and isopropyl alcohol (2.5 g) in the same manner as in Example 7 to provide 5-isopropyl 3-methyl (−)-2-cyano-6-methyl-4-(3-nitrophenyl)-1,4-dihydropyridine-3,5-dicarboxylate (4.9 g).

m.p.: 120°–122° C.

$[\alpha]_D^{20}$: −219.6° (c=1.0, CH$_3$OH),

NMR (CDCl$_3$, δ): 1.09 (3H, d, J=6.5 Hz), 1.25 (3H, d, J=6.5 Hz), 2.39 (3H, s), 3.78 (3H, s), 4.98 (1H, heptet, J=6.5 Hz), 5.19 (1H, s), 7.0 (1H, broad s), 7.25–7.76 (2H, m), 7.96–8.21 (2H, m)

Elemental analysis: for C$_{19}$H$_{19}$H$_3$O$_6$: Calcd.: C 59.22; H 4.97; N 10.90; Found : C 59.17; H 4.92; N 10.91;

What is claimed is:

1. A method for improving inner ear microcirculation, which comprises administering an effective amount of a dihydropyridine compound of the general formula:

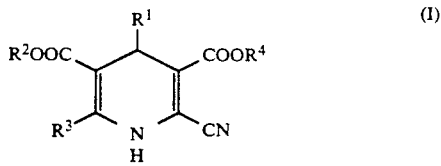

wherein R$^1$ is a nitrophenyl group; and
R$^2$, R$^3$ and R$^4$ each is a lower alkyl group, or a pharmaceutically acceptable salt thereof to a human or animal in need thereof.

2. A method for treating deafness or dizziness, which comprises administering an effective amount of the dihydropyridine compound (I) of claim 1 or a pharmaceutically acceptable salt thereof to a human or animal is need thereof.

3. The method of claim 1 or 2, wherein the dihydropyridine compound (I) is isopropyl 6-cyano-5-methoxycarbonyl-2-methyl-4-(3-nitrophenyl)-1,4-dihydropyridine-3-carboxylate.

* * * * *